United States Patent [19]
Passeron et al.

[11] Patent Number: 5,788,978
[45] Date of Patent: Aug. 4, 1998

[54] INJECTABLE PULSATILE IVERMECTIN COMPOSITION

[76] Inventors: Eduardo Julio Passeron, Tupac Amar''1180, Vincente Lopez-BS.AS., Argentina, 1634; Alberto Atilio Gellon, Melián 3257, Buenos Aires, Argentina, 1430; Elbio Humberto Taroni, Suipacha 1111, Buenos Aires, Argentina, 1008

[21] Appl. No.: 768,296

[22] Filed: Dec. 17, 1996

[51] Int. Cl.$^6$ .................................................. A61K 9/08
[52] U.S. Cl. .................. 424/426; 424/422; 424/489; 514/772.3; 514/774; 514/776
[58] Field of Search .................. 424/426, 422, 424/489; 514/772.3, 774, 776

[56] References Cited

U.S. PATENT DOCUMENTS

| | | | |
|---|---|---|---|
| 4,916,120 | 4/1990 | Roben | 514/30 |
| 5,446,070 | 8/1995 | Mantelle | 514/772.6 |
| 5,603,955 | 2/1997 | Gehrke | 24/484 |
| 5,645,856 | 7/1997 | Lacy | 424/455 |

FOREIGN PATENT DOCUMENTS

| | | |
|---|---|---|
| 0269921 | 6/1988 | European Pat. Off. . |
| 0413538 | 2/1991 | European Pat. Off. . |

OTHER PUBLICATIONS

"Ivermectin: A Potent New Antiparasitic Agent" by W. Campbell et al.; Science, vol. 221, pp. 823–828, Aug. 26, 1983.

"Sustained Drug Release Capsules for Ruminants" by Eckenhoff et al.; Ger. Offen. DE 3,509,410 (26 Sep. 1985); (Chemical Abstracts vol. 104, 1986, p. 446.).

"Controlled Release of Bioactive Agents from Lactide/Glycolide Polymers", Danny H. Lewis in Biodegradable Polymers as Drug Delivery Systems editors Mark Chasin & Robert Langer, Marcel Dekker, Inc. New York 1990.

"Gelatin Microspheres as drug Carrier Systems" Richard C. Oppenheim in Polymers, in: Controlled Drug Delivery editors Lisbeth Illum & Stanley S. Davis, Wright, Bristol 1987.

"Liquid Chromatographic Determination of Ivermectin in Bovine Serum" Oehler et al.; U.S. Dept. of Agriculture, Agricultural Research Service, U.S. Livestock Insects Laboratory, Kerrville, Texas; J. Assoc. Off. Anal. Chem. (vol. 72, No. 1, 1989).

Shih C. et al., J. of Controlled Release (1993), 25 (1–2), pp. 155–162.

Zingerman J., et al., Proc. Int. Symp. Controlled Release Bioact. Mater., (1992), 19$^{th}$, pp. 82–83.

*Primary Examiner*—Thurman K. Page
*Assistant Examiner*—D. Faulkner
*Attorney, Agent, or Firm*—Brumbaugh, Graves, Donohue & Raymond

[57] ABSTRACT

An injectable ivermectin composition having a programmable release rate and providing multiple concentration peaks of active ivermectin to produce a sequence of ivermectin release pulses into the blood of cattle and horses. The composition comprises a solution of 0.2%–10% w/w of ivermectin in a solvent selected from propyleneglycol and a mixture of glycerile caprylate, caproate and caprate, such as glycerides of caproic, caprilic and capric acids in equal parts. The solution is used as a vehicle for suspending microspheres 100 nm–200 μm in diameter of a degradable polymer containing between 0.5% and 50% of ivermectin. The microspheres may be formed from polylactic acid, polyglycolic acid or a copolymer of polylactic-polyglycolic acid. The programmable multi-pulse release system may also be obtained with a biodegradable matrix selected from hardenable natural polymers, such as gelatin or albumin, apart from the copolymers of lactic and gycolic acids. The polymers may be subjected to a hardening process to increase resistance to biological agents, for example, a solution of glutaraldehyde or alum or by heating the proteins up to coagulation temperature. In one embodiment, gelatin microspheres loaded with ivermectin are treated in an acqueous solution of glutaraldehyde at 25% during 24 hours and then suspended in the solvent. Another embodiment includes a suspension of ivermectin-loaded microspheres of DL-lactic-glycolic 1:1 copolymer. This monomer ratio may be altered to enhance resistance to erosion.

11 Claims, No Drawings

INJECTABLE PULSATILE IVERMECTIN COMPOSITION

FIELD OF THE INVENTION

The present invention concerns an injectable pharmaceutical ivermectin composition. This endoectopesticide has been outstanding for several years now for veterinary treatment, in particular for cattle and horses, in view of its good performance and therapeutic harmlessness in eliminating both internal and external parasites.

BACKGROUND OF THE INVENTION

The usual injectable preparations comprise solutions of ivermectin in different solvents. Such preparations generate ivermectin concentrations in the blood of treated animals ranging from just a few nanogrammes to several hundred nanogrammes per milliliter of serum.

Ever since ivermectin appeared on the veterinary market and because of the great success it enjoyed from the start, the prior art has been busy searching for solvents which would enable preparing injectable ivermectin solutions providing longer release times than the original formulations, which guaranteed 14 days efficiency. These new preparations looked to maintain ivermectin levels in the blood of treated animals for a longer period of time above a minimum efficiency level of 2 to 5 nanogrammes per milliliter of serum, since a therapeutically efficient level of ivermectin during a lengthly period of time keeps the treated animal free of parasites, enhancing its health and fattening rate this way.

It is therefore evident that the longer the animal is kept free of parasites the greater the effect of the treatment. Hence it is understandable that substantial efforts have been put in to devise injectable formulations, implants, ruminal devices, ointments and other pharmaceutical forms to this end.

SUMMARY OF THE PRIOR ART

It is known that ivermectin dissolved in propyleneglycol solvent releases into the blood during a period up to 14 days. Reference may be made to European Patent (EP) application 0045 655 (filed on 10 Feb. 1982) which discloses a preparation of ivermectin in glicerol-formal and propyleneglycol to increase the duration of the pesticide activity.

Reference may be made to other attempts at extending the activity of ivermectin in injectable formulations. For instance, EP application 00413 538 filed on 9 Feb. 1991 discloses using triacetine in injectable ivermectin formulations. This document claims that said formulations last 42 days and furthermore confirms that the activity of preexistent formulations lasted 14 days only.

None of the prior art documents known to us has claimed activity for injectable formulations lasting more than the 42-day period claimed by the aforesaid EP application 00413 538. Moreover, although the most diverse solvents as well as implantable matrices and ruminal boli having extended duration have been suggested, we know of no injectable preparation that may provide a sustained release of ivermectin from the solvent during an extended period of time and, in addition, provide release peaks lasting 15 to 20 days, the beginning of which may be programmed to follow the moment that the active drug reserve is practically completely exhausted in the solvent.

BRIEF DESCRIPTION OF THE INVENTION

Therefore, an object of the present invention is to provide an injectable pharmaceutical composition of ivermectin having a programmable release rate and capable of generating two or more concentration peaks of the active ivermectin substance, to thus produce two or more corresponding ivermectin release pulses, the beginnings of which may be separated by programmable time intervals of 10 to 30 days, each pulse of bioavailability of ivermectin lasting between 15 and 20 days, resulting in an overall ivermectin release period substantially longer than obtained heretofore.

During our investigations with this object in mind, we unexpectably found that upon preparation of a solution of ivermectin in a solvent selected from propyleneglycol and a mixture of glycerile caprylate, caproate and caprate, wherein the concentration of ivermectin in the solvent ranges between 0.5% and 10% w/w (by weight), an excellent vehicle was obtained for suspending microparticles therein, specially microspheres of a diameter between 100 nanometers and 200 micrometers, of a degradable polymer containing between 0.5% and 50% of ivermectin. Hence a heterogenous system is obtained, comprising a solution of ivermectin and a suspension of microparticles, enabling the release rate of ivermectin to be fully regulated in a reproducible manner and for a very extended period.

We have discovered that the initial period may be extended to up to 40 days using a special solvent formed by the glycerides of caproic, caprilic and capric acids in equal parts, and dissolving therein ivermectin at a concentration of between 0.2 and 7%.

We further found that an advantageous release system may be obtained by suspending predetermined microparticles in a solution of ivermectin, in particular microspheres loaded with ivermactine, regardless of the solvent used.

Some polymers known per se that have shown to be very useful for forming the forementioned microparticles or microspheres are polylactic acid, polyglycolic acid or a copolymer of polylactic-polyglycolic acid, wherein the ratio of polylactic acid to polyglycolic acid ranges between 0:1 and 1:0. As is well known, these polymers further offer the valuable advantage in a long-term injectable formulation of being fully biodegradable.

Because ivermectin is insoluble in acqueous media and because the solvent wherein the microspheres are suspended is saturated with dissolved ivermectin, there is only minimum diffusion of ivermectin from the microparticles containing the same towards the solvent and the microsphere content is released through erosion of the polymeric matrix once injected.

We have found that, in order to obtain a programmable release system, specially a system providing several release pulses, the biodegradable matrix may also be selected from natural polymers susceptible to hardening, in particular gelatin or albumin, apart from the above-mentioned copolymers of lactic and gycolic acids. Said polymers may be subjected to physical or chemical hardening processes to increase their resistance to biological agents responsible for the degradation in vivo thereof. In this way, the time the microparticles loaded with ivermectin may resist the action of enzymes and other eroding agents inside the body of animals before starting to release their contents may be extended within certain limits.

Such hardening processes are carried out by methods well known in the art, for example, by means of a solution of glutaraldehyde, solution of alum and other chemical agents or by heating the proteins up to coagulation temperature. For instance, the gelatin microspheres loaded with ivermectin may be subjected to treatment in an acqueous solution of glutaraldehyde at 25% during 24 hours and then suspended in any of the aforementioned solvents; the result is a system releasing ivermectin 40 to 60 days after the formulation is injected into the animal. A similar injectable formulation with a same ivermectin liberation profile is obtained by suspending ivermectin-loaded microspheres of DL-lactic-glycolic 1:1 copolymer. In this way, by suspending the ivermectin-loaded particles in a solution of ivermectin, a system is obtained wherein in a first phase ivermectin is released from the solvent for a period lasting between 20 and 40 days, depending on the selected solvent, followed by a second phase between days 40 and 60 after injection during which ivermectin is released from the gelatin microparticles or the lactic-glycolic copolymer. The second phase may last from 15 to 25 days such that the system achieves an overall ivermectin release period of 55 to 85 days.

The experts in the art may easily compute for themselves conditions and intensities of the microparticle hardening process required to obtain systems releasing ivermectin for periods in excess of 80 days, say after 100 or 120 days. Such hardening processes are known per se. In a similar fashion, it is possible to choose a monomer ratio in the lactic-glycolic copolymer microspheres to obtain greater resistance to erosion than with a 1:1 monomer ratio.

Thus, it is possible according to the present invention to obtain an injectable ivermectin solution containing microparticles which have undergone different hardening treatments or have been obtained with copolymers formed from different monomer ratios, in order to produce subsets of suspended microparticles such that each subset differs in the biodegradability resistance thereof. In this way, the resulting formulations generate three or more ivermectin release pulses, the starting point of each separated by programmable time intervals, for example from 10 to 30 days separation between pulses having a duration of 15 to 40 days of ivermectin bioavailability, such that the overall therapeutically efficient treatment period may be substantially longer than 100 days.

The invention may be better understood but not restricted in its scope by reference to the following detailed examples:

EXAMPLE 1

A like volume of propeleneglycol was added to a solution of gelatin in water having a 10% concentration. Thereafter a solution of 11% of ivermectin in propyleneglycol was added in a proportion of 1 volume of ivermectin solution for every 3 volumes of gelatin solution.

The resulting solution was dripped slowly into a suitable volume of vaseline which was stirred strongly using a propellor-type stirrer at 700 RPM. Stirring continued for 1 hour after all the solution had been added and thereafter 5 ml of an acqueous solution of glutaraldehyde at 25% was added and stirring continued for 16 more hours.

Once stirring had been completed, the suspension was filtered and the microspheres were successively washed in petroleum ether and alcohol and suspended in a solution of ivermectin at 2% in a mixture comprising glycerile caprylate, caproate and caprate in equal parts, in doses such that each milliliter of suspension contained 20 milligrammes of ivermectin dissolved therein and 20 milligrammes of ivermectin loaded into microspheres incorporated into the formulation.

This formulation was administered subcutaneously to the animals to be treated at a rate of 1 milliliter per 100 kg of animal weight.

EXAMPLE 2

Field Test of the formulation expressed in Example 1.

Groups comprising 50 to 60 bovine heads each of the same sex, breed and approximate age were identified with eartags. The animals were weighed and a selection was made of three groups of 14 animals each such that in each group the average weight did not differ by more than 5 kg from the overall average weight and that the standard deviations of the average weights were substantially alike. Treatments were randomly assigned to each group, as follows:

Treatment 1: Each animal was administered the dose of the formulation of Example 1 corresponding to its weight.

Treatment 2: Each animal was administered a corresponding dose of a commercial ivermectin formulation.

Treatment 3: Each animal was administered a volume of solvent of the formulation of Example 1 in a dose corresponding to the dose it would receive of said formulation according to its weight.

All treatments were injected subcutaneously on the same day. Samples of 40 milliliters of blood were extracted from each animal into tubes labelled with each animal's number on the days indicated in Table I herein. In the case of Treatment 3 (control), blood samples were taken on the first day only, to make sure that none of the control animals had been injected with ivermectin by mistake. Samples of fecal matter were aseptically taken from each animal before the injections (Table I, second column) and on the same days the blood samples were taken.

The blood samples were left to coagulate, centrifuged and each subjected to a test to determine the amounts (in ng/ml) of ivermectin in serum according to J. Pivnichny et al. J. Pharm. Sci., p. 1,447, vol. 72 (1983). The individual results of each group were averaged and the average results tabulated in Table I. The fecal matter samples were counted for parasite eggs (per gramme). The averages of each treatment are tabulated in Table I.

TABLE I

| Day: | Pre inj. | 1 | 5 | 10 | 15 | 20 | 30 | 40 | 50 | 60 | 70 | 80 | 90 |
|---|---|---|---|---|---|---|---|---|---|---|---|---|---|
| Treatment 1 | | | | | | | | | | | | | |
| Ivermectin: | | 70 | 40 | 20 | 12 | 10 | 7 | 5 | 95 | 70 | 15 | 3 | 0 |
| Eggs/gram: | 335 | 33 | 4 | 2 | 0 | 0 | 0 | 0 | 2 | 0 | 0 | 0 | 12 |
| Treatment 2 | | | | | | | | | | | | | |
| Ivermectin: | | 102 | 32 | 14 | 3 | 6 | 0 | 0 | 0 | 0 | 0 | 0 | 0 |
| Eggs/gram: | 227 | 15 | 4 | 2 | 0 | 0 | 0 | 10 | 7 | 39 | 70 | 101 | 180 |

TABLE I-continued

| Day: | Pre inj. | 1 | 5 | 10 | 15 | 20 | 30 | 40 | 50 | 60 | 70 | 80 | 90 |
|---|---|---|---|---|---|---|---|---|---|---|---|---|---|
| Treatment 3 | | | | | | | | | | | | | |
| Ivermectin: | | 0 | | | | | | | | | | | |
| Eggs: | 192 | 180 | 201 | 217 | 320 | 208 | 185 | 300 | 395 | 327 | 405 | 372 | 383 |

EXAMPLE 3

3 grammes of DL-lactide-co-glycolide having a molecular weight of 7.000 and 0.75 grammes of ivermectin were dissolved in 60 milliliters of methylene chloride. The resulting solution was slowly dripped into a solution of 2.03 grammes of polyvynilic alcohol in 750 milliliters of distilled water, strongly stirred with a palette-type stirrer at 250 RPM. Stirring was continued for six hours while the solution was exposed to an air current at 28° to 45° C. generated by a blower having a heater resistor. Once this period was over, the suspension was left to sediment and the microspheres were filtered and dried in a vacuum.

A formulation was prepared suspending a number of microspheres worth 20 milligrammes of ivermectin in each milliliter of a solution of ivermectin at 2% in propyleneglycol.

An injectable formulation was prepared suspending in a solution of ivermectin at 2% in the solvent indicated in Example 1 the number of 16-hour hardened microspheres required to contain 20 mg of ivermectin per milliliter of suspension and of 32-hour hardened microspheres required to contain 20 mg of ivermectin per milliliter of suspension.

EXAMPLE 6

Field Test of the formulation expressed in Example 5.

The formulation of Example 5 was injected into each animal at the rate of 1 milliliter per 100 kg of animal weight. The field test was carried out in the same way as example 4.

Table III hereinbelow displays the results achieved.

TABLE III

| Day: | Pre inj. | 1 | 5 | 15 | 20 | 30 | 40 | 50 | 60 | 70 | 80 | 90 | 100 | 110 | 120 |
|---|---|---|---|---|---|---|---|---|---|---|---|---|---|---|---|
| Ivermectin | | 96 | 52 | 30 | 12 | 6 | 3 | 0 | 121 | 57 | 12 | 0 | 75 | 36 | 12 |
| Eggs: | 402 | 97 | 4 | 0 | 6 | 3 | 0 | 2 | 30 | 0 | 0 | 0 | 4 | 0 | 0 |

EXAMPLE 4

Field Test of the formulation expressed in Example 3.

The field test was carried out on a group of Aberdeen Angus calves weighing an average of 200 kg. The formulation of Example 3 was injected in each animal at the rate of 1 milliliter per 100 kg of animal weight.

The results are set out in Table II hereinbelow (wherein the amount of ivermectin is indicated in ng/ml of blood and parasite eggs in quantity per gramme of dung).

EXAMPLE 7

Field Test.

Microparticles of DL-lactide-co-glycolide copolymer having a molecular weight of 7.000, wherein the ratio of each monomer is chosen to provide a 1:1 relationship, loaded with 25% w/w of ivermectin were uniformly suspended in a 2% solution of ivermectin in the solvent of example 1, to obtain a suspension of 20 milligrammes of suspended ivermectin per milliliter of suspension. This suspension was injected in a group comprising 6 steers (treatment 1). A commercial ivermectin formulation (known

TABLE II

| Day: | Pre inj. | 1 | 5 | 10 | 15 | 20 | 30 | 40 | 50 | 60 | 70 | 80 | 90 |
|---|---|---|---|---|---|---|---|---|---|---|---|---|---|
| Ivermectin: | | 50 | 30 | 17 | 10 | 4 | 0 | 0 | 12 | 109 | 66 | 30 | 9 |
| Eggs/gram: | 447 | 230 | 3 | 4 | 0 | 0 | 0 | 6 | 4 | 0 | 0 | 4 | 0 |

EXAMPLE 5

Microspheres were prepared according to the schedule of Example 1 but doubling the quantity. The dry microspheres were separated into two groups. Both groups were hardened according to the schedule of Example 1 except that the second group was treated for twice as long.

by its trademark "IVOMEC") was injected in the recommended dose in another group comprising 4 steers (treatment 2). The average weight of the animals in each group was 361 kg and 400 kg, respectively. The results are shown in Table IV hereinbelow (in ng of ivermectin/ml of blood and parasite eggs/gramme of dung).

TABLE IV

| Day: | Pre inj. | 1 | 5 | 11 | 15 | 20 | 30 | 34 | 41 | 48 | 55 | 62 |
|---|---|---|---|---|---|---|---|---|---|---|---|---|
| Treatment 1 | | | | | | | | | | | | |
| Ivermectin: | | 95 | 60 | 40 | 30 | 17 | 10 | 7 | 5 | 105 | 54 | 20 |
| Eggs/gramme: | 343 | 20 | 5 | 0 | 0 | 4 | 0 | 2 | 10 | 0 | 0 | 0 |
| Treatment 2 | | | | | | | | | | | | |
| Ivermectin: | | 70 | 41 | 7 | 5 | 0 | 0 | 0 | 0 | 0 | 0 | 0 |
| Eggs/gramme: | 407 | 390 | 10 | 0 | 0 | 3 | 0 | 10 | 50 | 90 | 80 | 220 |

EXAMPLE 8

Field Test.

An additional load of DL-lactide-co-glycolide microspheres, obtained from a 65:35 monomer ratio of DL-lactide-glycolide having a molecular weight of 9,500, and 25% w/w of ivermectin, was added to a formulation identical to that described in example 7 in an amount sufficient to produce an additional 20 milligrammes of ivermectin per milliliter of suspension. Twelve steers weighing an average of 250 kg were injected with a dose of 1 ml suspension per 100 kg steer-weight. An equivalent volume of solvent was injected into a control group comprising another twelve steers weighing an average of 230 kg. The results are shown in Table V hereinbelow (in ng of ivermectin/ml of blood and parasite eggs/gramme of dung).

TABLE V

| Day: | Pre inj. | 1 | 10 | 20 | 32 | 39 | 49 | 60 | 70 | 80 | 90 | 100 | 110 | 120 |
|---|---|---|---|---|---|---|---|---|---|---|---|---|---|---|
| Treatment 1 | | | | | | | | | | | | | | |
| Ivermectin: | | 70 | 50 | 40 | 20 | 5 | 75 | 30 | 10 | 0 | 92 | 70 | 14 | 0 |
| Eggs/gr: | 368 | 40 | 0 | 0 | 0 | 2 | 0 | 4 | 0 | 0 | 10 | 4 | 0 | 0 |
| Control | | | | | | | | | | | | | | |
| Ivermectin: | | 0 | | | | | | | | | | | | |
| Eggs/gr: | 240 | 360 | 350 | 450 | 310 | 300 | 250 | 500 | 500 | 450 | 600 | 610 | 450 | 500 |

We claim:

1. A pharmaceutical composition for injecting ivermectin in a programmable releasable manner generating in the blood of an animal at least two peaks of concentration of the active ivermectin substance; said composition comprising a solution of ivermectin in a solvent selected between propyleneglycol and a mixture of glycerile caprate, caprylate and caproate; wherein the concentration of ivermectin in said solvent is between 0.5% and 7% weight/weight and wherein said solution is a vehicle carrying microparticles in suspension therein, specially microspheres of a biodegradable polymer containing between 0.5% and 50% of ivermectin.

2. A pharmaceutical composition according to claim 1, wherein the ivermectin solvent is propyleneglycol and the ivermectin is released into the blood for a period between 0 and 14 days.

3. A pharmaceutical composition according to claim 1, wherein the ivermectin solvent is a mixture of glycerides of capric; caprylic and caproic acids in a concentration between 10 and 80% weight/weight and wherein the ivermectin is released into the blood during a period of between 0 and 40 days.

4. A pharmaceutical composition according to claim 1, wherein said biodegradable polymer is selected from L or DL polylactic acid, polyglycolic acid and a copolymer of L or DL polylactic-polyglycolic acid, wherein the ratio of polylactic acid to polyglycolic acid ranges between 0:1 and 1:0.

5. A pharmaceutical composition according to claim 1, wherein said biodegradable polymer is a natural polymer which may be hardened, specially gelatin or albumin.

6. A pharmaceutical composition according to claim 5, wherein said biodegradable, hardenable polymer has been subjected to a chemical or physical hardening process, in particular been hardened in a solution of glutaraldehyde.

7. A pharmaceutical composition according to claim 1, wherein the biodegradable polymer that forms the microspheres in suspension is a protein which has been subjected to a hardening treatment, in particular been hardened in a solution of glutaraldehyde at a concentration of 7% to 25% for between 0.1 and 40hours, whereby between 5 and 60 days after the formulation has been injected, said microspheres begin to release the contents thereof during a second phase of bioavailability having a duration of between 5 and 30 days from the beginning of this second pulse, thereby providing an overall period of between 35 and 90 days wherein ivermectin is released.

8. A pharmaceutical composition according to claim 7, further comprising additional ivermectin-loaded microspheres which have been subjected to a more intense hardening treatment providing greater resistance to biodegradation, whereby said composition generates at least three pulses of ivermectin separated by time intervals of between 5 and 60 days, each bioavailability pulse having a duration of between 5 and 30 days, thereby providing an overall period in excess of 100 days wherein ivermectin is released.

9. A pharmaceutical composition according to claim 4, wherein said biodegradable polymer is L- or DL-polylactic-co-polyglycolide at a monomer ratio of 1:1 and having a molecular weight between 4,000 and 12,000, whereby between 40 and 60 days after the composition has been injected said microspheres begin to release their ivermectin load during a second bioavailability phase lasting between 5 and 30 days from the beginning of this second pulse, whereby the overall ivermectin release period of the composition is between 45 and 90 days.

10. A pharmaceutical composition according to claim 9, wherein said biodedegradable polymer further comprises additional sets of ivermectin-loaded microspheres formed of DL- or L-polylactic-co-polyglycolide at monomer ratios of 5:95 to 95:5 and having molecular weights between 4,000 and 12,000, thereby generating upon injection additional pulses releasing ivermectin, the beginning of said pulses separated by programmable time-intervals of between 5 and 60 days, each pulse lasting between 5 and 30 days from the beginning of this second pulse, whereby the overall ivermectin release period of the composition is substantially greater than 100 days.

11. A pharmaceutical composition according to claim 10, wherein the ivermectin solvent is propyleneglycol and the ivermectin is initially released from said solution into the blood for a period between 0 and 14 days.

\* \* \* \* \*